(12) United States Patent
Ikeda et al.

(10) Patent No.: US 6,416,641 B1
(45) Date of Patent: Jul. 9, 2002

(54) BIOSENSOR

(75) Inventors: Shin Ikeda, Katano; Motokazu Watanabe, Kadoma; Toshihiko Yoshioka; Shiro Nankai, both of Hirakata, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/328,511

(22) Filed: Jun. 9, 1999

(30) Foreign Application Priority Data

Jun. 11, 1998 (JP) .......................................... 10-163243

(51) Int. Cl.⁷ .......................................... G01N 27/327
(52) U.S. Cl. .................................... 204/403; 205/777.5
(58) Field of Search ................................ 204/403, 416; 205/777.5

(56) References Cited

U.S. PATENT DOCUMENTS

| | | | |
|---|---|---|---|
| 4,053,381 A | * | 10/1977 | Hamblen et al. ............ 204/416 |
| 4,689,136 A | * | 8/1987 | Nakajima et al. ........... 204/426 |
| 5,108,564 A | * | 4/1992 | Szuminsky et al. | |
| 5,437,999 A | | 8/1995 | Diebold et al. |
| 5,759,364 A | | 6/1998 | Charlton et al. |
| 5,916,425 A | * | 6/1999 | Leader et al. ............... 204/416 |

FOREIGN PATENT DOCUMENTS

| EP | 0 284 518 A2 | | 9/1988 |
|---|---|---|---|
| EP | 0351891 | * | 1/1990 |
| JP | 60244853 | * | 12/1985 |
| JP | 61002060 | * | 1/1986 |
| JP | 03202764 | | 4/1991 |
| JP | 9-101280 | | 4/1997 |
| JP | 10-170471 | | 6/1998 |
| WO | WO 98/35225 | | 8/1998 |

* cited by examiner

Primary Examiner—T. Tung
(74) Attorney, Agent, or Firm—McDermott, Wll & Emery

(57) ABSTRACT

The present invention relates to a biosensor comprising a working electrode base plate 11, a counter electrode base plate 14 and a reagent layer containing at least an enzyme and an electron mediator, wherein a working electrode 12 disposed on the working electrode base plate and a counter electrode 15 disposed on the counter electrode base plate are positioned so as to mutually face and a terminal of a measuring device can be brought in contact with terminals 13, 16 of both electrodes from through-holes 25, 24. Such a biosensor can produce highly reliable and accurate measuring results with only a small amount of a sample.

8 Claims, 6 Drawing Sheets

BIOSENSOR

BACKGROUND OF THE INVENTION

The present invention relates to a biosensor for facilitating a prompt and highly accurate quantitation of a substrate contained in a sample.

Conventionally, polarimetry, colorimetry, reductometry and other methods using various chromatography have been proposed as a method for quantitative analysis of sugars such as sucrose and glucose. These methods, however, are of poor accuracy, since their specificity toward sugars is not so high. Of these methods, polarimetry, whose operation is rather simple, is greatly influenced by the temperature during the operation, therefore, is not appropriate as a method which enables ordinary people to make an easy quantitation of sugars at home.

Recently, various types of biosensors utilizing specific catalysis of enzymes have been developed.

The following describes quantitation of glucose as an example of quantitating a substrate contained in a sample solution. The method of using glucose oxidase (EC1.1.3.4: hereinafter referred to as "GOD") and an oxygen electrode or a hydrogen peroxide electrode is widely known in the art as electrochemical quantitation of glucose (for example, "BIOSENSOR" edited by Shuichi Suzuki, Kodan-sha).

GOD selectively oxidizes substrate β-D-glucose to D-glucono-δ-lactone, using oxygen as an electron mediator. In the presence of oxygen, oxygen is reduced into hydrogen peroxide during this oxidation by GOD. The decreased amount of oxygen is measured by the oxygen electrode, or otherwise, the increased amount of hydrogen peroxide is measured by the hydrogen peroxide electrode. Since both the decreased amount of oxygen and the increased amount of hydrogen peroxide are in proportion to the amount of glucose contained in a sample solution, the quantitation of glucose can be made from either of these amounts.

As inferred from the reacting process, this method has a defect that the results of measurement are largely affected by the concentration of oxygen contained in the sample solution. Moreover, the measurement becomes impossible in case of the absence of oxygen in the sample solution.

Therefore, a new type of glucose sensor substituting an organic compound such as potassium ferricyanide, a ferrocene derivative or a quinone derivative or a metal complex for oxygen as an electron mediator has been developed. With this type of sensor, by oxidizing a reductant of the electron mediator produced as the result of the enzyme reaction on the electrode, the concentration of glucose contained in the sample solution can be obtained based on the oxidation current. The substitution of such an organic compound or a metal complex for oxygen as an electron mediator makes it possible to form a reaction layer wherein known amounts of GOD and the electron mediator therefore are stably and accurately carried on the electrode. In this case, since the reaction layer, with its condition almost dry, can also be integrated with the electrode system, a disposable glucose sensor based on this art has recently drawn a lot of attention. The typical example of this sensor is the biosensor disclosed in Japanese patent publication No. 2517153. The disposable glucose sensor facilitates easy measurement of glucose concentration by simply introducing a sample solution into the sensor which is detachably connected to a measuring device. This method is applicable to not only quantitation of glucose but quantitation of any other substrate contained in the sample solution.

In the measurement using above-mentioned glucose sensor, the concentration of substrate contained in the sample solution can easily be detected with a small amount of sample solution (several $\mu l$). However, a high-performance, easy-to-handle biosensor which would enable measurement with a much smaller amount, in particular 1 $\mu l$ or less of sample solution is anxiously expected to be developed in various fields in recent years.

Also, a conventional electrochemical glucose sensor comprises an electrode system disposed on single plane in most of the cases. If the electrode system is on single plane and an extremely small amount of sample solution is used, the resistance to charge-transfer between electrodes, mainly ion transfer, is increased so that a variance in the results of the measurement may be caused.

SUMMARY OF THE INVENTION

In order to solve above problems, the biosensor in accordance with the present invention comprises a working electrode base plate, a counter electrode base plate and a reagent layer containing at least an enzyme and an electron mediator, wherein a working electrode disposed on said working electrode base plate and a counter electrode disposed on said counter electrode base plate are positioned so as to mutually face having a space therebetween.

In other words, the working electrode and the counter electrode are opposed to each other via an opening space. To form such an opening space, at least one of these base plates may have a curved portion, a concave portion or the like.

The present invention provides a biosensor comprising a working electrode base plate, a counter electrode base plate, a spacer member placed between said both base plates and a reagent layer containing at least an enzyme and an electron mediator, wherein a working electrode disposed on said working electrode base plate and a counter electrode disposed on said counter electrode base plate are positioned so as to mutually face with a spacer member placed therebetween.

In this case, it is preferable that at least one of said working electrode base plate and said counter electrode base plate has a through-hole which exposes an electrode terminal of the other plate to outside.

Namely, when the working electrode base plate has the through-hole, an electrode terminal of the counter electrode is exposed to outside. And, when the counter electrode base plate has the through-hole, an electrode terminal of the working electrode is exposed to outside. Of course, both base plates may have the through-holes.

It is preferable that one of said working electrode base plate and said counter electrode base plate has a cut-away portion which exposes an electrode terminal of the base other plate to outside and that a lead connected to the electrode on a surface of the base plate having a cut-away portion extends, via a side surface of the base plate having the cut-away portion, to the back of the surface where the lead is connected.

Also, it is preferable that one of said working electrode base plate and said counter electrode base plate has a through-hole filled with a conductive material and a cut-away portion which exposes an electrode terminal of the other base plate to outside and that a lead connected to the electrode on a surface of the base plate having the cut-away portion extends, via the conductive material, to the back of the surface where the lead is connected.

The present invention provides a biosensor comprising an insulating base plate provided with a groove on its surface, a cover member jointed to said insulating base plate to form a space for accommodating a sample in said groove, a working electrode and a counter electrode disposed so as to mutually face in said groove and a reagent layer containing at least an enzyme and an electron mediator disposed in said groove.

DETAILED DESCRIPTION OF THE INVENTION

In the following, the present invention is described in detail referring to embodiments.

Embodiment 1

As an example of biosensor, glucose sensor is explained.

Figure 1:
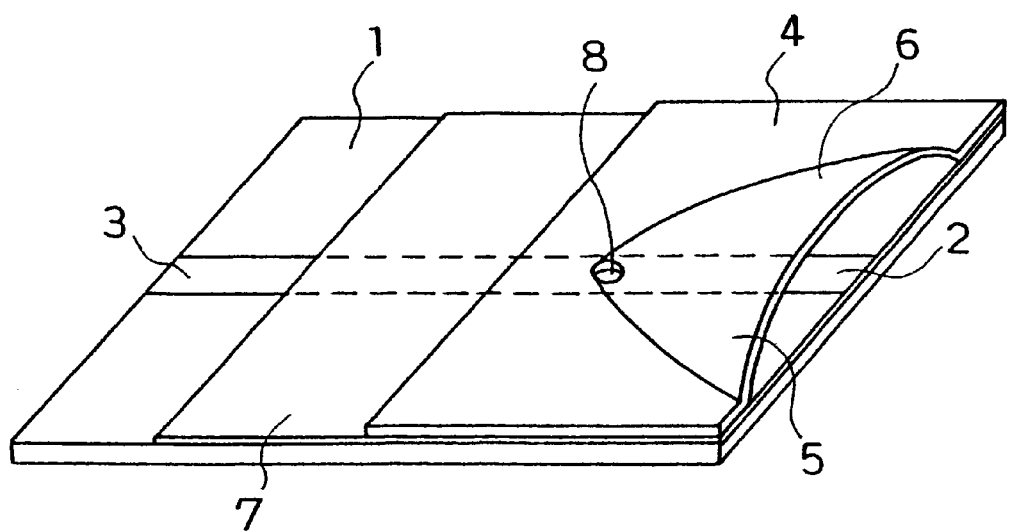
FIG. 1 is an oblique perspective view of a glucose sensor in accordance with one embodiment of the present invention.

FIG. 1 describes the appearance of a glucose sensor in accordance with one embodiment of the present invention.

A working electrode base plate 1 was made as follows. Palladium was sputtered on an insulating base plate to form a working electrode and a lead/terminal portion. Then, an insulating member 7 was attached to the base plate to form a working electrode 2 and a terminal 3 which was inserted into a measuring device.

Meanwhile, by using an insulating base plate with a curved portion 6 which was bloated toward outside, palladium was sputtered on the internal concave wall of said curved portion 6 to form a counter electrode 5. This was how a counter electrode base plate 4 was formed. The end of the curved portion was provided with an air vent 8.

An aqueous solution containing GOD and potassium ferricyanide which was an electron mediator was dropped on the working electrode 2 on the working electrode base plate 1, then dried to form a reagent layer.

Lastly, the working electrode base plate 1 and the counter electrode base plate 4 were laminated to produce a glucose sensor. By this lamination, the working electrode 2 and the counter electrode 5 were disposed so as to mutually face having a space between the working electrode base plate 1 and the curved portion 6. This space accommodated a sample, and if a sample solution was brought in contact with the open end of this space, a capillary phenomenon moved the sample solution toward the air vent to reach the electrode system.

An aqueous solution containing a predetermined amount of glucose was supplied as a sample to the space of the sensor. After a predetermined time, a voltage of 500 mV was applied to the working electrode 2 using the counter electrode 5 as reference. As for the counter electrode 5, electrical conductivity was obtained by fastening the end of the curved portion 6 with a clip, for example. When the value of the current which flowed between the working electrode and the counter electrode by this voltage application was measured, the current response in proportion to the glucose concentration in the solution was observed. Glucose reacted with ferricyanide ion and GOD in the solution and, as the result, glucose was oxidized to glucono lactone while reducing ferricyanide ions to ferrocyanide ions. The concentration of this ferrocyanide was in proportion to the glucose concentration. Thus, the glucose concentration could be measured based on the oxidation current.

Compared to the case where almost equal amount of a sample was introduced to the sensor comprising an electrode system disposed on single plane of a base plate, an increase in the response value was observed in this embodiment. This is presumed because the electrode system was disposed so as to mutually face so that ion transfer between the electrodes is facilitated.

Embodiment 2

Figure 2:
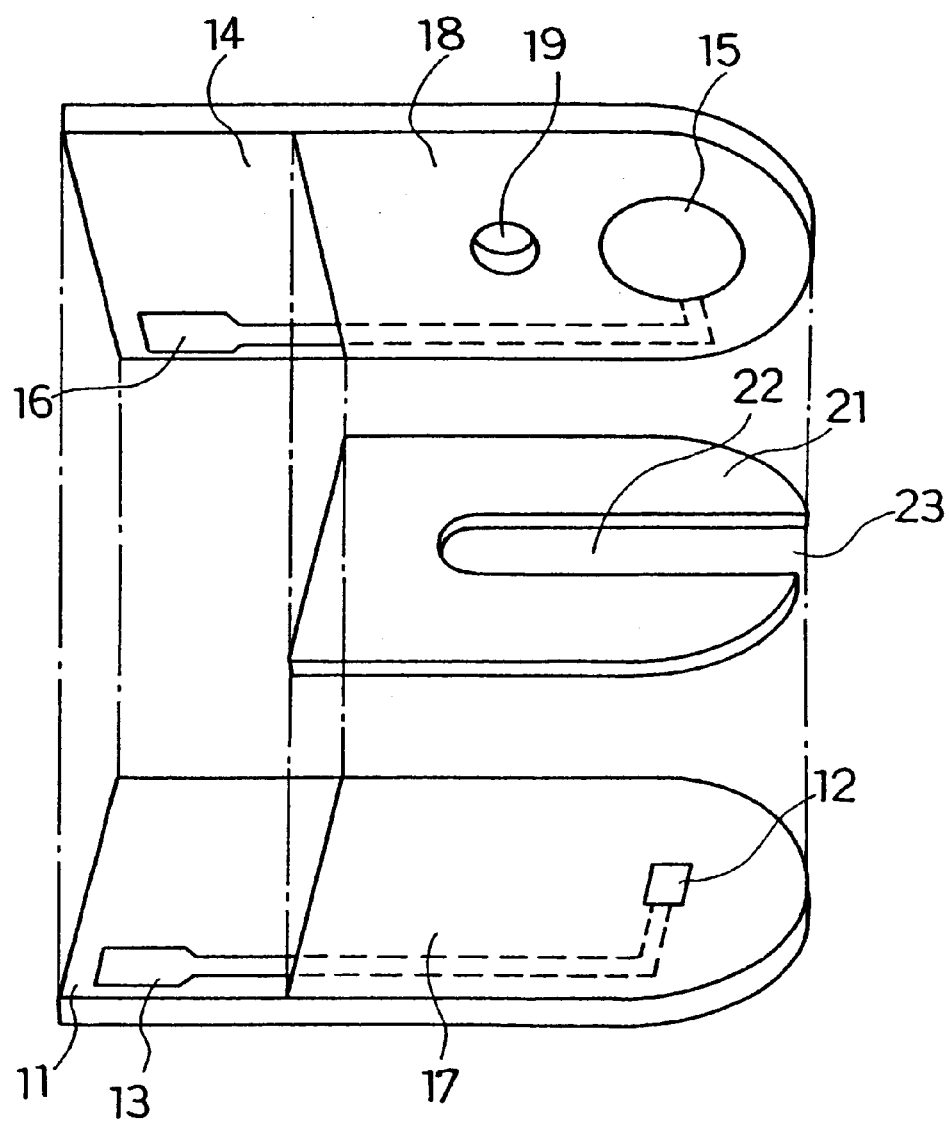
FIG. 2 is a broken oblique perspective view of a glucose sensor in accordance with another embodiment of the present invention.

FIG. 2 is a broken oblique perspective view of a glucose sensor in accordance with the embodiment of the present invention with an omission of a reagent layer, and shows one example of the arrangement of electrode/lead.

A working electrode base plate 11 was made as follows. First, a silver paste was screen-printed on an insulating base plate of polyethylene terephthalate to form a lead 13. Then, a conductive carbon paste containing a resin binder was printed on the base plate to form a working electrode 12, which was in contact with the lead 13. Subsequently, an insulating paste was printed on the base plate 11 to form an insulating layer 17, which covered the peripheral portion of the working electrode 12 so as to hold the exposed area of the working electrode 12 constant.

In the same manner as described above, a counter electrode base plate 14 was made. Specifically, after a silver paste was printed on the backside of an insulating base plate to form a lead 16, a conductive carbon paste was printed to form a counter electrode 15 and an insulating paste was printed to form an insulating layer 18. The counter electrode base plate was provided with an air vent 19.

A spacer 21 placed between the working electrode base plate 11 and the counter electrode base plate 14 had provided with a slit 22, which formed a sample solution supply pathway between the working electrode base plate and the counter electrode base plate.

In the same manner as the embodiment 1, a reagent layer was formed on the working electrode base plate. Then, the working electrode base plate 11, the counter electrode base plate 14 and the spacer 21 were adhered to each other in a positional relationship as shown by the dotted line in FIG. 2 to produce a biosensor. The counter electrode and the working electrode having the reagent layer thus faced each other in the sample solution supply pathway formed at the slit 22 of the spacer 21. The air vent 19 of the counter electrode base plate was connected to this sample solution supply pathway. Thus, if a sample solution was brought in contact with a sample solution supply inlet 23 formed on the open end of the slit, a capillary phenomenon caused the sample solution to reach the reagent layer in the sample solution supply pathway.

Then, glucose was measured in the same manner as the embodiment 1.

The strength of sensor against physical pressure applied to the base plate was increased by the placement of the spacer between the both base plates. Thus, the volume of the sample solution supply pathway was easily kept constant, so that the influence of physical pressure and the like on the sensor response was diminished.

As the result of measurement, a current response in proportion to the glucose concentration contained in the solution was observed and a variance in the response was reduced.

Embodiment 3

Figure 3:
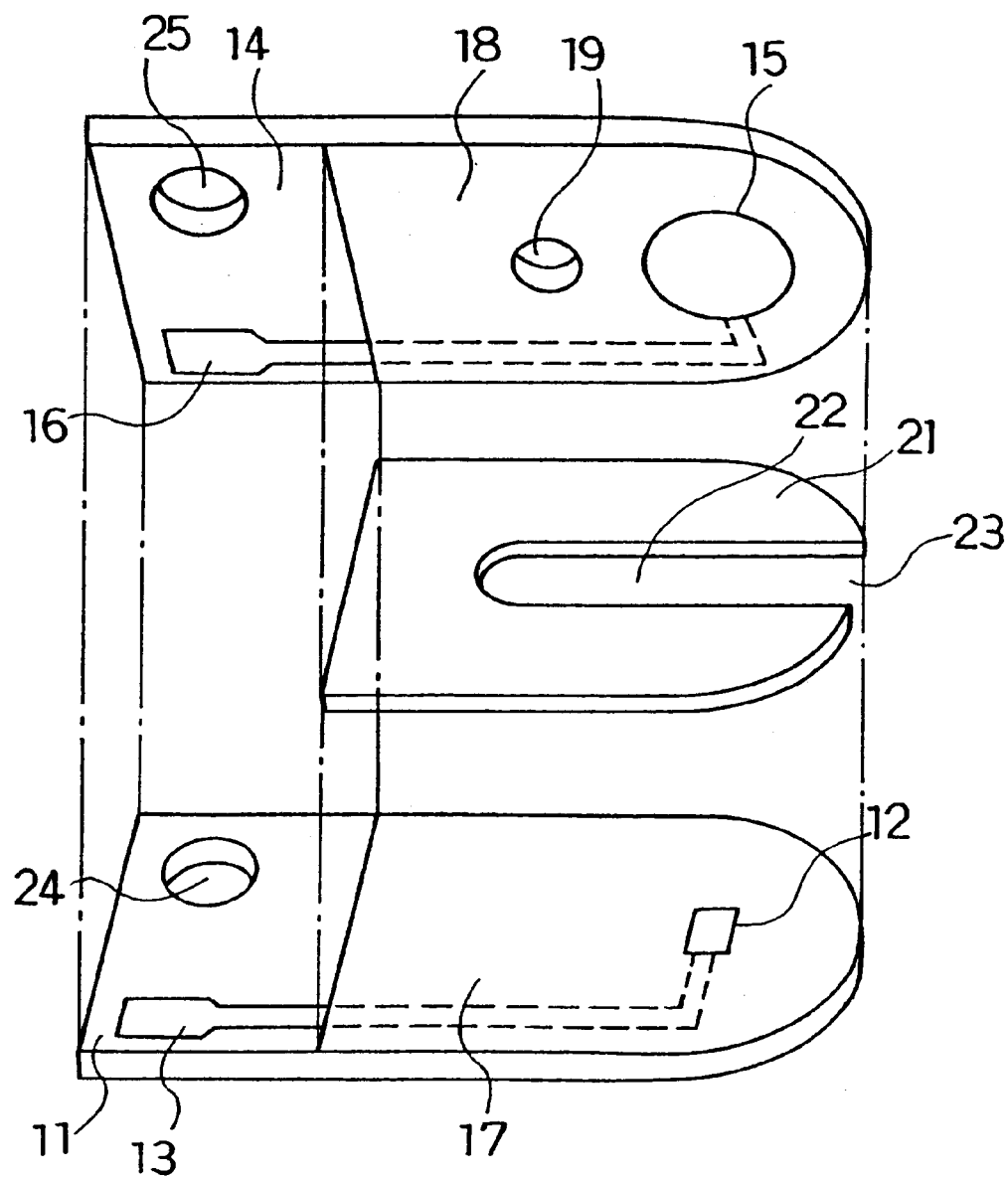
FIG. 3 is a broken oblique perspective view of a glucose sensor in accordance with still another embodiment of the present invention.

FIG. 3 is a broken oblique perspective view of a glucose sensor in accordance with the embodiment of the present invention with an omission of a reagent layer.

This sensor had the same configuration as the embodiment 2 except that the working electrode base plate 11 and the counter electrode base plate 14 respectively had a through-hole 24 and 25 for exposing a terminal to outside.

By the provision of a through-hole to each of both base plates, a part of lead/terminal 16 of the counter electrode base plate 14 was exposed to outside from the through-hole 24 of the working electrode base plate 11, while a part of lead/terminal 13 of the working electrode base plate 11 was exposed to outside from the through-hole 25 of the counter electrode base plate 14. If the spacer 21 would horizontally extend to the terminals, the spacer might be provided with a corresponding through-hole.

This provision of the through-hole secured the fitting of a laminating-type sensor chip into the measuring device, i.e., the electrical connection of the sensor chip and the measuring device, which lead to the improvement in the measuring accuracy.

Embodiment 4

Figure 4:
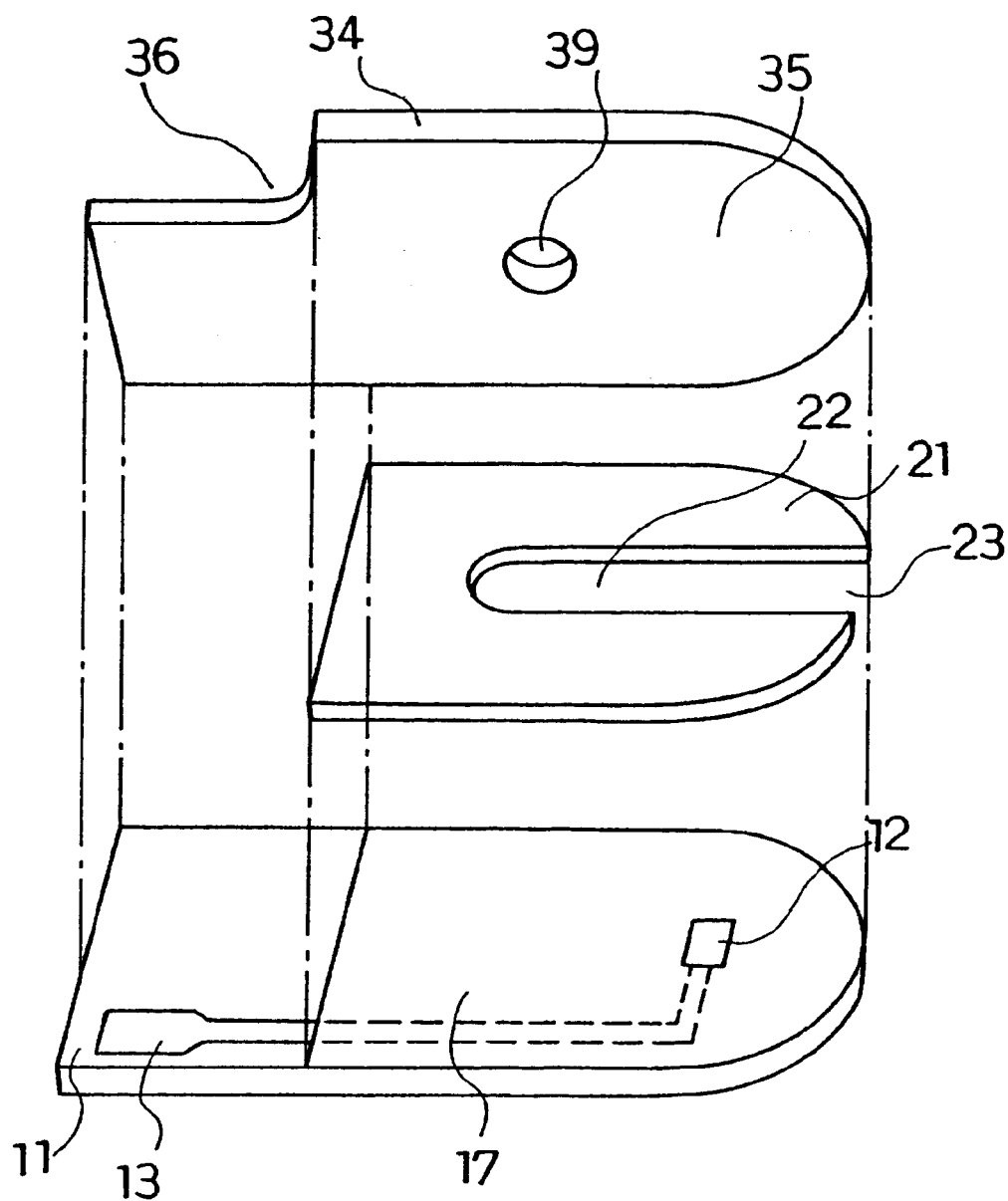
FIG. 4 is a broken oblique perspective view of a glucose sensor in accordance with another embodiment of the present invention.

FIG. 4 is a broken oblique perspective view of a glucose sensor in accordance with the embodiment of the present invention with an omission of a reagent layer.

A working electrode base plate 11 and a spacer 21 had the same configuration of the embodiment 2.

On the other hand, a counter electrode base plate 34 was formed as follows. Palladium was sputtered on the whole surfaces (including the sides) of an Insulating base plate provided with a cut-away portion 36, which was formed by cutting away the portion corresponding to a terminal 13 of the working electrode base plate 11. A palladium layer thus formed under the counter electrode base plate 34 functioned as a counter electrode, which was electrically connected to the terminal of the palladium layer formed on the side and the upper surface of the base plate.

In the same manner as the embodiment 1, a reagent layer was formed on the working electrode of the working electrode base plate. Then, the working electrode base plate 11, the counter electrode base plate 34 having an air vent 39 and the spacer 21 were adhered to each other in a positional relationship as shown by the dotted line in FIG. 4, to produce a biosensor.

By the provision of the cut-away portion 36 to the counter electrode base plate 34, a part of lead/terminal of the working electrode base plate 11 was exposed to outside from the cut-away portion 36. If the spacer 21 would horizontally extend to the position corresponding to the terminals, the spacer 21 might be provided with a corresponding cut-away portion. Meanwhile, the lead electrically connected to the counter electrode 35 extended via the side of the counter electrode base plate 34 to the upper surface thereof.

This enabled both terminals to be exposed to outside of only one base plate. Therefore, the conventional connecting terminal of the measuring device widely used could be applied to the sensors of above-mentioned configuration without making any changes thereon, which was effective for reducing the manufacturing cost of sensors.

Figure 5:
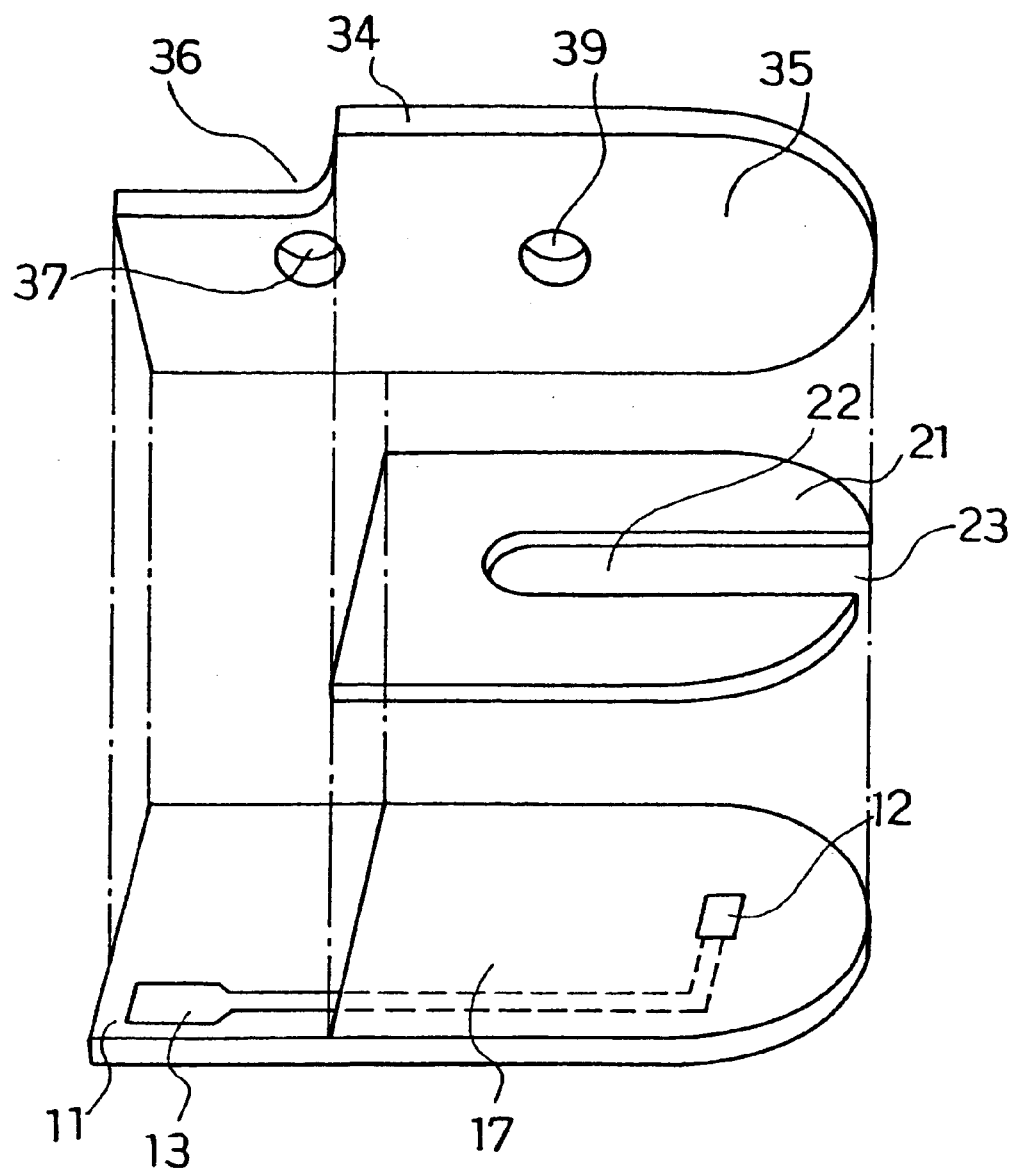
FIG. 5 is a broken oblique perspective view of a glucose sensor in accordance with still another embodiment of the present invention.

A lead disposed on a side of a sheet-like base plate might have a problem of physical strength, compared to a lead disposed on a upper surface of the plate or under the plate. In such a case, as shown in FIG. 5, it was also possible that the counter electrode base plate 34 might be provided with a through-hole 37 filled with a conductive material such as a silver paste, a carbon paste or the like. Then, the lead of the electrode disposed under the base plate might be connected via this conductive material to the terminal on the base plate.

In this embodiment, the counter electrode base plate 34 was provided with the cut-away portion 36 or the through-hole 37, however, even if the working electrode base plate 11 might be provided with these cut-away portion and through-hole, the same effects could be obtained. In this case, it would be required to determine the area of the counter electrode using an insulating layer and so forth.

Embodiment 5

Figure 6:
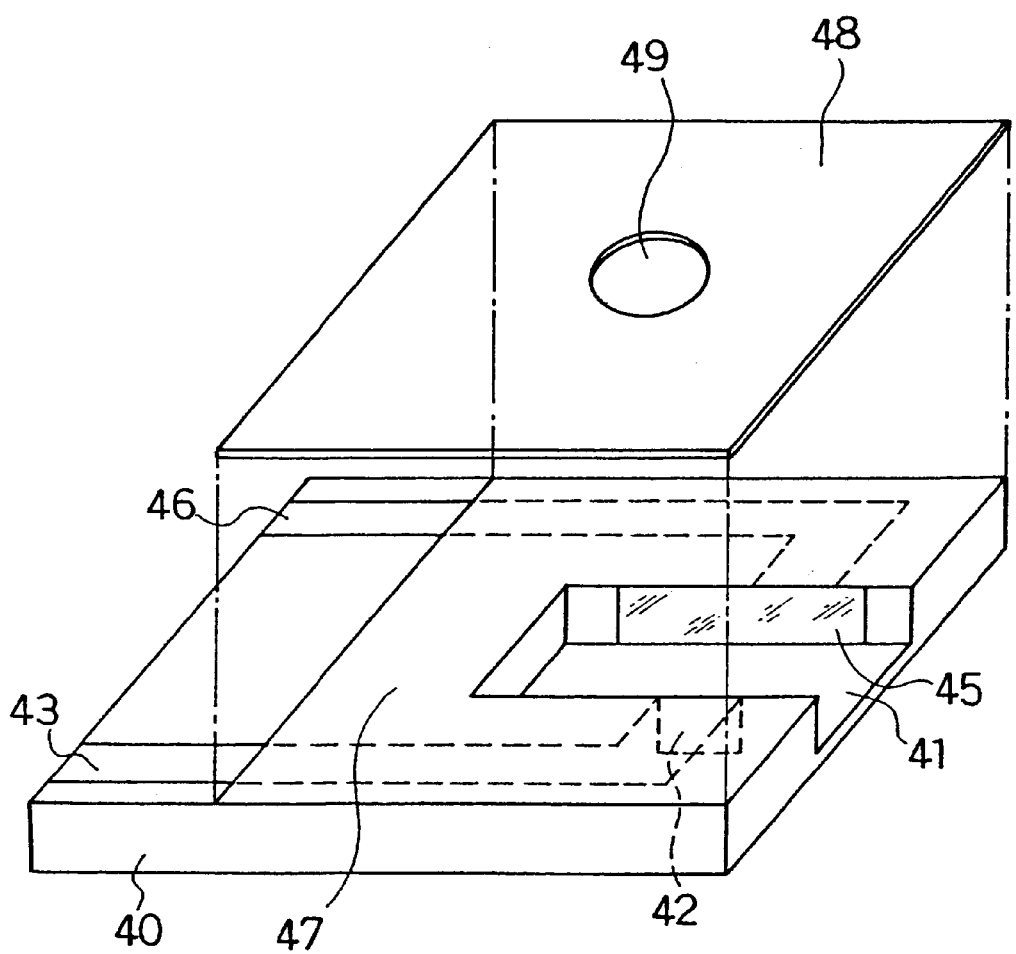
FIG. 6 is a broken oblique perspective view of a glucose sensor in accordance with another embodiment of the present invention.

FIG. 6 is a broken oblique perspective view of glucose sensor in accordance with the embodiment of the present invention with an omission of a reagent layer.

An insulating base plate 40 was provided with a groove 41 whose outer surface and upper surface were open. Palladium was sputtered on the side walls facing each other of the groove 41 and a upper surface of the insulating base plate. And the base plate was trimmed by laser to form a working electrode 42, a counter electrode 45 and lead/terminal portions 43 and 46 corresponding with each electrode. Also, an insulating layer 47 was formed so as to partially cover the said lead. Next, an aqueous solution containing GOD and potassium ferricyanide was dropped on the groove 41 and dried to form a reagent layer. Thereafter, a cover 48 provided with an air vent 49 at a position corresponding to the innermost of the groove was adhered to the base plate 40 in a positional relationship as shown by the dotted line in FIG. 6 to produce a biosensor.

In this biosensor, the groove 41 of the base plate was the place where a sample was accommodated, and if a sample solution was brought in contact with the open end of the groove 41 on the end of the base plate, a capillary phenomenon moved the sample solution toward the air vent to reach both electrodes.

As for the sensors such as above-mentioned embodiments wherein both base plates having an electrode were laminated, a discrepancy in position of the base plates might occur in their laminating process. However, as for the sensor of this embodiment wherein electrode systems were formed on the internal wall of the groove 41, such discrepancy induced by laminating process did not occur, thereby not causing a decline of measuring accuracy.

The voltage applied to the electrode system in the above-mentioned embodiments was 500 mV, but might not be limited thereto if the voltage might cause the oxidization of the electron mediator which is reduced in the enzyme reaction.

As the oxidoreductase contained in the reaction layer, the one corresponding to a substrate to be analyzed contained in the sample solution can be used. For this purpose, fructose dehydrogenase, glucose oxidase, alcohol oxidase, lactic acid oxidase, cholesterol oxidase, xanthine osidase and amino acid oxidase are exemplified.

As the electron mediator, potassium ferricyanide, p-benzoquinone, phenazine methosulfate, methylen blue and ferrocene derivatives are exemplified. Also, oxygen can be used as the electron mediator to obtain current response. One or more of these electron mediators are used.

The enzyme or the electron mediator may not be dissolved in the sample solution when the reagent layer is fixed to the base plate. In case it is fixed, Cross-linking method or Absorption method is preferable. They may be blended into electrode materials.

In the above embodiments, the through-hole and the cut-away portion provided to the base plate were described in order to bring a specific electrode system, lead/terminal and the connecting terminal of the measuring device in contact with said terminal, however, their shape, arrangement and so forth are not limited to those described in the embodiments.

Also, in the above embodiments, carbon and palladium are used as electrode materials, however, electrode materials are not limited to those. As working electrode materials, any conductive materials can be used so long as they themselves are not oxidized at the time of oxidization of the electron mediator. As counter electrode materials, any conductive materials such as silver or platinum which is generally used can be used.

The present invention, as mentioned above, provides a biosensor which can produce highly reliable and accurate measuring results with only a small amount of a sample.

What is claimed is:

1. A biosensor comprising:
   a working electrode base plate,
   a counter electrode base plate having a curved section,
   a reagent layer containing at least an enzyme and an electron mediator,
   a working electrode disposed on said working electrode base plate, and
   a counter electrode disposed on said counter electrode base plate,
   said working electrode and said counter electrode being positioned so as to mutually face one another with a space between the electrodes, said space being formed by the curved section of said counter electrode base plate.

2. A biosensor comprising:
   a working electrode base plate,
   a counter electrode base plate having a bottom surface, an upper surface and a side surface, said counter electrode base plate having a cut-away portion which provides access to an electrode terminal on the working electrode base plate through the counter electrode base plate,
   a spacer member disposed between said working electrode base plate and said counter electrode base plate, and
   a reagent layer containing at least an enzyme and an electron mediator,
   a working electrode disposed on said working electrode base plate, and
   a counter electrode disposed on said counter electrode base plate, said counter electrode being disposed on said bottom surface of said counter electrode base plate,
   said working electrode and said counter electrode being disposed on opposite sides of said spacer member,
   wherein at least a portion of at least one of said side surface and said upper surface of said counter electrode base plate being operative as an electrode terminal of the counter electrode.

3. The biosensor in accordance with claim 2, wherein said counter electrode is electrically connected to said upper surface via said side surface.

4. The biosensor in accordance with claim 2, wherein said counter electrode base plate has a through-hole filled with a conductive material for electrically connecting said counter electrode to said upper surface.

5. A biosensor comprising:
   an insulating plate provided with a groove on its surface, said groove having a first side wall and a second side wall, said first side wall and said second side wall opposing one another,
   a cover member coupled to said insulating base plate, said insulating plate and said cover member forming a space for accommodating a sample in said groove,
   a working electrode formed in said insulating plate, and
   a counter electrode formed in said insulating plate, said working electrode being disposed in said first side wall of said groove and said counter electrode being disposed in said second side wall of said groove, such that said working electrode and said counter electrode face one another,
   and a reagent layer containing at least an enzyme and an electron mediator disposed in said groove.

6. The biosensor of claim 5, wherein said cover member further comprises an air vent disposed in a position corresponding to an inner most portion of said groove.

7. A biosensor comprising:
   a working electrode base plate,
   a counter electrode base plate having an upper surface, a bottom surface and a side surface,
   a spacer member disposed between said working electrode base plate and said counter electrode base plate, and
   a reagent layer containing at least an enzyme and an electron mediator,
   a working electrode disposed on said working electrode base plate, and
   a counter electrode disposed on said counter electrode base plate, said counter electrode being disposed on said bottom surface of said counter electrode base plate,
   said working electrode and said counter electrode are disposed on opposite sides of said spacer member,
   said counter electrode base plate having a through-hole formed therein which is filled with a conductive material, said conductive material contacting said counter electrode, and
   said counter electrode base plate having a cut-away portion which provides access to an electrode terminal on the working base plate through the counter electrode base plate.

8. The biosensor of claim 7, wherein a first lead is coupled to said electrode terminal on the working base plate, and a second lead is coupled to the conductive material, both said first lead and said second lead being exposed to the upper surface of said counter electrode base plate.

* * * * *